United States Patent
van Dijk et al.

(10) Patent No.: US 10,206,594 B2
(45) Date of Patent: Feb. 19, 2019

(54) MEASURING DEVICE AND METHOD FOR MEASURING PHYSIOLOGICAL DATA OF A MAMMAL

(71) Applicant: N.V. Nederlandsche Apparatenfabriek NEDAP, DC Groenlo (NL)

(72) Inventors: Jeroen Martin van Dijk, DC Groenlo (NL); Jan Cornelis Stekelenburg, DC Groenlo (NL); Derk Jan Roosenboom, DC Groenlo (NL)

(73) Assignee: N.V. NEDERLANDSCHE APPARATENFABRIEK NEDAP, Groenlo (NL)

( * ) Notice: Subject to any disclaimer, the term of this patent is extended or adjusted under 35 U.S.C. 154(b) by 362 days.

(21) Appl. No.: 15/287,938

(22) Filed: Oct. 7, 2016

(65) Prior Publication Data

US 2017/0100045 A1    Apr. 13, 2017

(30) Foreign Application Priority Data

Oct. 7, 2015    (NL) ...................................... 2015582

(51) Int. Cl.
*A61B 5/1455*    (2006.01)
*A61B 5/024*    (2006.01)
(Continued)

(52) U.S. Cl.
CPC .......... *A61B 5/02427* (2013.01); *A61B 5/021* (2013.01); *A61B 5/02416* (2013.01);
(Continued)

(58) Field of Classification Search
CPC ............ G06K 7/10158; A61B 5/02427; A61B 5/021; A61B 5/02416; A61B 5/1455;
(Continued)

(56) References Cited

U.S. PATENT DOCUMENTS

2003/0069486 A1    4/2003    Sueppel et al.
2005/0065414 A1*   3/2005    Allen .................... A01K 1/031
                                                                    600/310
(Continued)

FOREIGN PATENT DOCUMENTS

WO    2005/120335 A2    12/2005
WO    2014/210588 A1    12/2014

OTHER PUBLICATIONS

Dutch Search Report and the Written Opinion of the Dutch Search Report, dated May 25, 2016 (7 pages).

*Primary Examiner* — Eric Winakur
*Assistant Examiner* — Darin Janoschka
(74) *Attorney, Agent, or Firm* — Jacobson Holman, PLLC.

(57) ABSTRACT

A measuring device for measuring physiological data of a mammal comprising a measuring unit, to be worn by the mammal, with a first and second module. The first module comprises a light source and the second module comprises a sensor unit for measuring an intensity of a fraction of the light delivering a measuring signal. There is a synchronization means for pulsewise activating the light source synchronously with the second module, wherein the measuring signal is indicative of the value of the intensity measured during the pulsewise activation. The synchronization means comprises an energy transmitting unit and a detector which is part of the other one of the first and the second module, in an operating condition the energy transmitting unit pulsewise generates an electromagnetic field, and the detector receives this field and generates therefrom a supply voltage for use in that other module.

26 Claims, 5 Drawing Sheets

Figure 1:
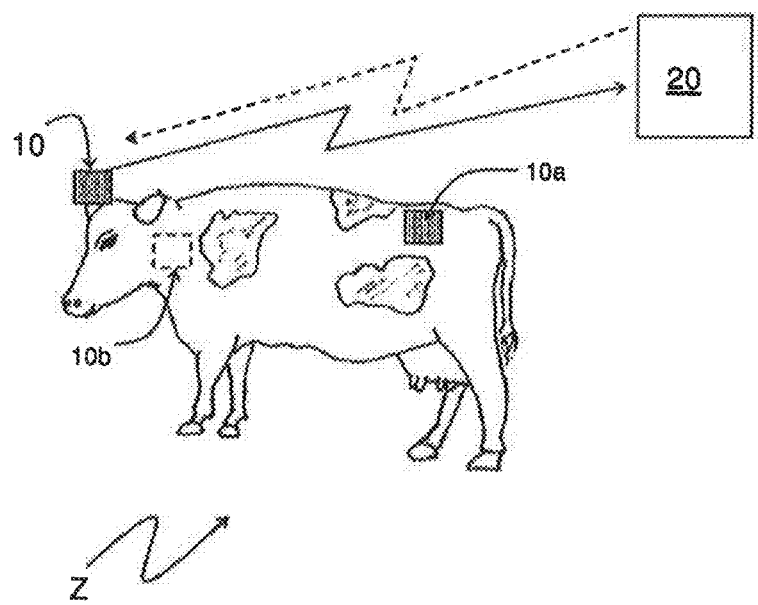

(51) Int. Cl.
*A61B 5/021* (2006.01)
*A61B 5/00* (2006.01)
*G06K 7/10* (2006.01)

(52) U.S. Cl.
CPC .......... *A61B 5/1455* (2013.01); *A61B 5/6801* (2013.01); *A61B 5/7235* (2013.01); *G06K 7/10158* (2013.01); *A61B 2503/40* (2013.01); *A61B 2560/0209* (2013.01)

(58) Field of Classification Search
CPC . A61B 5/6801; A61B 5/7235; A61B 2503/40; A61B 2560/0209
See application file for complete search history.

(56) References Cited

U.S. PATENT DOCUMENTS

2009/0240125 A1* 9/2009 Such ................. A61B 5/14552 600/323
2014/0378791 A1* 12/2014 DeHennis ............ A61B 5/0015 600/310

* cited by examiner

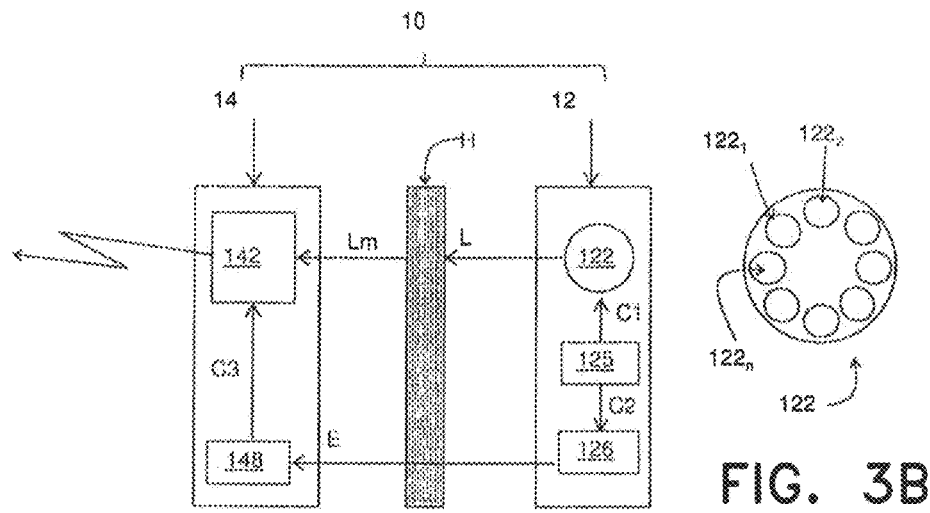
FIG. 3A
FIG. 3B
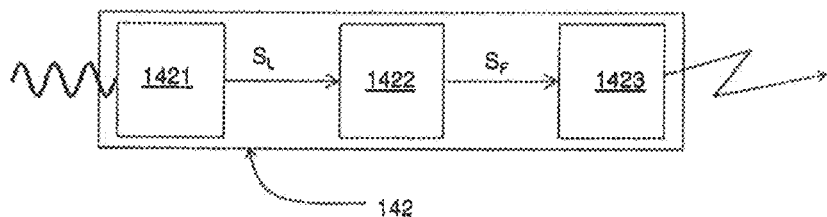
FIG. 4
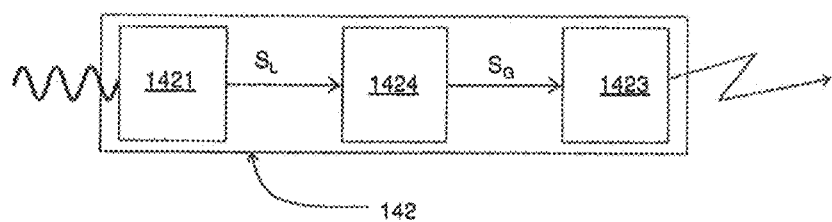
FIG. 5

MEASURING DEVICE AND METHOD FOR MEASURING PHYSIOLOGICAL DATA OF A MAMMAL

BACKGROUND OF THE INVENTION

The heartbeat of a mammal can be measured by determination of light absorption upon passage through the skin. For this purpose, for instance, on one side of the skin, light of a known intensity is generated, and on the opposite side the magnitude of the fraction of this light that is transmitted by the skin is measured. The measured fraction depends on inter alia the extent to which light en route is absorbed in the skin by the blood in the veins and capillaries in it. This, in turn, depends on inter alia the diameter of the veins and capillaries. This diameter varies periodically with the frequency of the heartbeat. Accordingly, the measured intensity also varies with that same frequency. This corresponding frequency of the intensity variations is then recorded and stored or forwarded for further processing.

CROSS-REFERENCE TO RELATED APPLICATIONS

"Not Applicable"

STATEMENT REGARDING FEDERALLY SPONSORED RESEARCH OR DEVELOPMENT

"Not Applicable"

THE NAMES OF THE PARTIES TO A JOINT RESEARCH AGREEMENT

"Not Applicable"

STATEMENT REGARDING PRIOR DISCLOSURES BY THE INVENTOR OR A JOINT INVENTOR

"Not Applicable"

Also for measuring the heartbeat of animals in a livestock, this in itself is an attractive method. It has been found, however, that in this case usually the extent of absorption is rather high, due to inter alia the presence of bodily hair. While this can be obviated by using a stronger light source, this requires a higher electrical power. This is not a major drawback if a mains supply is available. But if only a battery supply is available, as with a measuring device to be worn by the animal, the use of a stronger light source is at the expense of the useful life of the measuring device. Use of a more sensitive sensor is often not meaningful because it is also more sensitive to fluctuations present in the received light due to other causes, so that the signal-to-noise ratio remains unfavorable.

BRIEF SUMMARY OF THE INVENTION

It is an object of the invention to provide a measuring device having a relatively long useful life, for measuring physiological data, such as the heartbeat of the animal.

It is a further object of the invention to provide a measuring method for measuring data, such as the heartbeat of the animal, for a relatively long duration.

To realize the first-mentioned object, the invention provides a measuring device for measuring physiological data of a mammal for determining at least one condition parameter of the animal. The measuring device comprises a measuring unit to be worn by the mammal, having a first module and second module to be arranged mutually on opposite sides opposite a skin part of the mammal. The first module comprises a light source for generating light. The second module comprises a sensor unit for measuring an intensity of a fraction of the light received via that skin part and delivering a measuring signal that is indicative of the measured value of the intensity. The measuring device according to the invention is configured for pulsewise activating the light source, while the measuring signal is indicative of the value of the intensity measured during pulsewise activation. The measuring device is furthermore provided with synchronization means for synchronously activating the light source and the second module, the synchronization means comprising an energy transmitting unit which is part of one of the first and the second module and comprising a detector which is part of the other one of the first and the second module, while in an operative condition the energy transmitting unit pulsewise generates an electromagnetic field, and the detector receives this field and generates therefrom a supply voltage for use in that other module.

To realize the second object mentioned, the invention provides a measuring method for measuring physiological data of a mammal for determining at least one condition parameter of the animal. This measuring method comprises pulsewise generating light on one side of a skin part of the mammal and on an opposite side of that skin part measuring an intensity of a fraction of the generated light received via that skin part, wherein pulsewise generating the light and on the opposite side of that skin part measuring the fraction of the generated light received via the skin part are done synchronously by pulsewise generating an electromagnetic field, receiving the electromagnetic field, and generating a supply voltage from the received electromagnetic field.

The at least one condition parameter to be determined is, for example, a heartbeat of the animal or a blood pressure of the animal. Also, the condition parameter to be determined can be a blood value, i.e., an indication of a concentration of one or more constituents in the blood. Also, a combination of condition parameters can be established with the measuring device and/or the measuring method.

As with the measuring device and the measuring method according to the current invention the light used for the measurement is generated pulsewise, the intensity of the generated light can be raised without thereby also increasing the electrical energy consumption. Consequently, raising the intensity used does not need to be accompanied by a decrease of the useful life.

The pulse duration of the generated light can be, for example, 50% of the pulse period, being the time duration between two successive pulses, so that twice as strong a light source can be used without this leading to a decrease of the useful life. If desired, the pulse duration can be set to be even considerably shorter in proportion to the pulse period, for example, shorter than 0.1 times the pulse period, 0.01 times the pulse period, or shorter than 0.001 times the pulse period. This does not require the intensity of the light source to be chosen inversely proportionally higher to be able to carry out the measurement reliably. For instance, the pulse duration can be set to be 0.0001 times the duration of the pulse period, while a light source is used that is 100 times stronger. Thus, additionally, an extension of the useful life by a factor of 100 is achieved. The choice of the pulse period can depend on the nature of the physiological datum to be measured. If the heartbeat is a condition parameter to be determined of the animal, or one of the condition parameters, it is desired to choose a pulse period that is at the least twice shorter than the period of the expected slowest heartbeat. The pulse period can then, for instance, have a time duration in the order of magnitude of 2 Hz and higher.

The pulse duration can for instance be chosen in the order of magnitude from 1 to 100 microseconds.

A reduction of the consumption of electrical energy has been accomplished in that the sensor unit is activated synchronously with the light source of the first module. Synchronous activation allows a shorter pulse duration, thereby reducing the energy consumption.

The synchronization means comprise an energy transmitting unit for generating an electromagnetic field and a detector for detecting the electromagnetic field and generating therefrom a supply voltage. One of the first and the second module is then provided with the energy transmitting unit and a control unit for pulsewise activating the energy transmitting unit and other components of that module. The other module is then provided with the detector for supplying that other module with the supply voltage furnished. The energy captured by the detector activates the module in which it is included precisely at the moment at which the control unit also activates the components of the other module, so that a reliable synchronization of the two modules is realized. An additional advantage in that regard is that the module with the detector does not need any battery or the like.

In an embodiment, the energy transmitting unit is part of the second module and the detector is part of the first module, while the light source is operated with the generated supply voltage. It is expected that the first module with the light source has a relatively low energy requirement compared to that of the second module with the sensor. While the light source needs to be activated only shortly for the measurement, it may be that the second module still needs electrical energy during a subsequent time interval to process the measuring data. In this embodiment, in which the detector is part of the first module, therefore less energy needs to be transferred between the modules. Given the same efficiency of the wireless energy transfer, the losses in the energy transfer in this embodiment will be smaller than those in an embodiment in which the detector is part of the second module with this sensor.

In particular if the second module with the sensor unit is already provided with a processor for processing the measuring data, it is favorable that the energy transmitting unit is also part of this module, so that also the energy transmitting unit can be controlled with this same processor without the control signal needed to that effect first needing to be transferred to the other module.

In addition, it is favorable if any output means for outputting the data or the results obtained therefrom are included in the second module with the sensor. The output means can then receive the data or the results from the sensor or the processor directly with a signal guide.

In a typical embodiment the output means are an RFID modulator which can cooperate with an RFID transmitter in an RFID transmission system. The RFID transmitter used then generates an interrogation field, whereby the RFID modulator transfers information by modulating the interrogation field according to a pattern that corresponds to the information to be transferred, such as the identity of the measuring unit and/or measuring data and/or results obtained therefrom by processing. The RFID modulator can also draw energy from the interrogation field generated by the RFID transmitter. The RFID modulator can thus provide for its own energy requirement, but may also, for instance, charge an electric storage medium, such as a chargeable battery or a capacitor, from which the measuring unit can be fed. For this embodiment also, it is favorable if the energy transmitting unit is part of the second module and the detector is part of the first module, so that it is not necessary first to transfer energy from the RFID modulator in the second module to a storage medium included in the first module, and then to transfer energy again from that storage medium in the first module to the components of the second module.

It will be clear there are other options available for providing the modules with electrical energy, for example, a fixed battery in one or more of the two parts. Alternatively, one or more chargeable batteries can be used which are charged, for example, with a solar cell, or with a microgenerator that generates electricity from movements of the measuring unit caused by the mammal.

The measuring device and the method according to the invention are also suitable for measuring other condition parameters, such as the blood values, i.e., the concentration of specific constituents in the blood, such as different kinds of corpuscles, hormones, salts, e.g. calcium salts and the like. The values of these concentrations can be indicative of the animal's state of health. An increase of the concentration of white corpuscles, for example, can be indicative of an inflammation. If an iron content is too low, the animal has anemia. With a change of these concentrations, there is also a change of the absorption of light in the blood and the intensity measured on the basis thereof. By measuring the latter, it is possible to keep an eye on the animal's state of health and to treat the animal, if necessary, preventatively or curatively. Excepting extreme situations, these changes will take place on a time scale that is relatively long compared with the period of the heartbeat. Accordingly, the concentration measurements can be carried out with a pulse period that is considerably longer than that necessary for measuring the heartbeat. If the measuring device and/or the measuring method according to the invention are utilized exclusively for measuring blood values, then, for example, a pulse period of 1 time a day can suffice. Depending on the circumstances, a longer or shorter pulse period may be set. If an epidemic is prevalent and/or the animal in question is of poor health, it may for instance be chosen to use a shorter pulse period, for example a pulse period of an hour, or in acute situations a still shorter pulse period of, for example, a quarter of an hour or less, for example one minute. If the animal is in good health and there is no threat of an epidemic, also a period longer than a day, for example a period of a week, could be set.

BRIEF DESCRIPTION OF THE SEVERAL VIEWS OF THE DRAWING(S)

Figure 2:
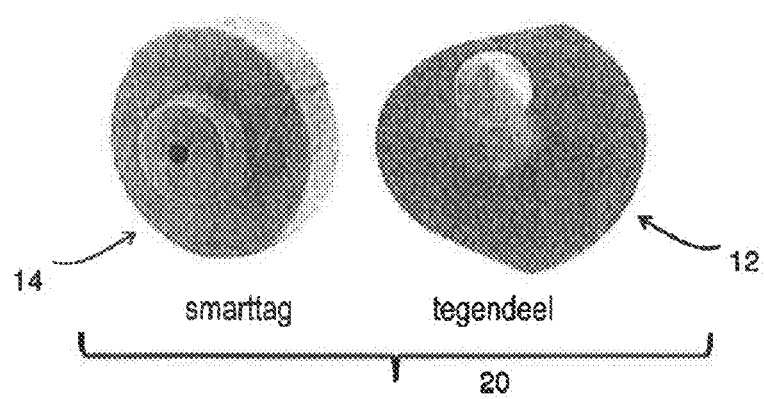
Figure 6:
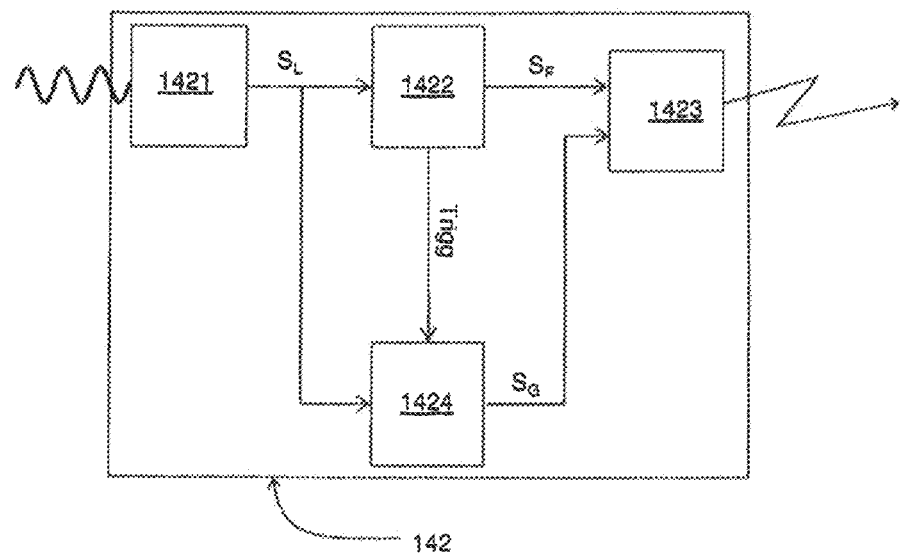
Figure 7:
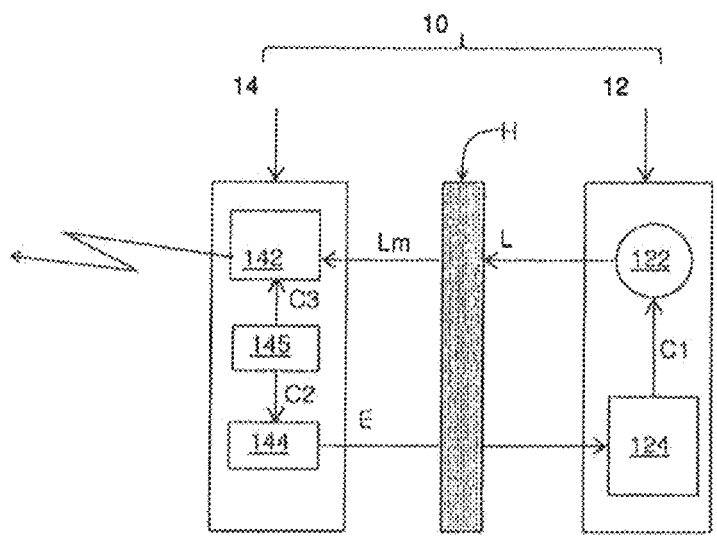
Figure 8:
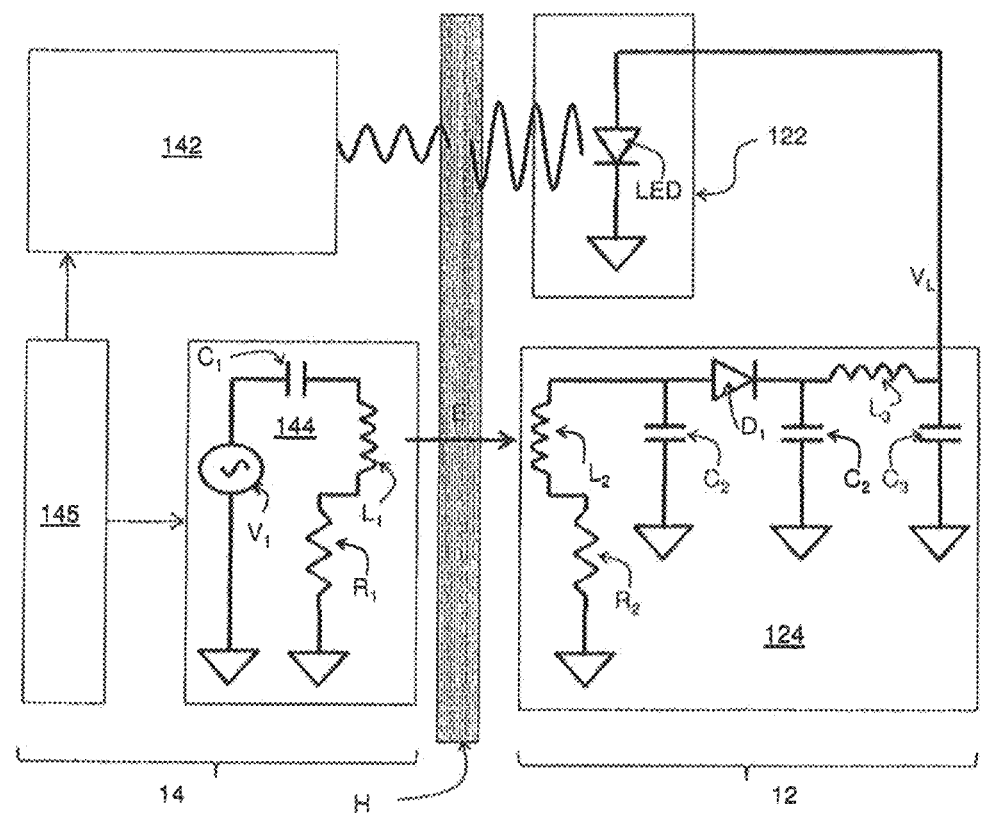

These and other aspects of the invention are further explained below on the basis of the drawings. In the drawings:

FIG. 1 schematically shows a system for measuring physiological data of a mammal Z, FIG. 2 shows a practical implementation of a measuring unit, being part of an embodiment of the system of FIG. 1, FIG. 3 consists of 3A and 3B:

FIG. 3A schematically shows components of the measuring unit of FIG. 2,

FIG. 3B shows an embodiment of a part of one of the components in more detail, FIG. 4 shows a first component of the measuring unit in more detail, FIG. 5 shows an alternative design of the first component of the measuring unit in more detail, FIG. 6 shows another alternative design of the first component of the measuring unit in more detail, FIG. 7 schematically shows components of an alternative embodiment of the measuring unit of FIG. 2, FIG. 8 shows components of FIG. 7 in more detail, FIG. 9 consists of 9A, 9B and 9C, illustrating a measuring method according to the invention.

DETAILED DESCRIPTION OF THE INVENTION

In the following figures corresponding parts have the same reference numerals.

FIG. 1 schematically shows a system for measuring physiological data of a mammal Z for determining at least one condition parameter of the mammal Z. The system comprises a measuring unit 10, 10a, 10b to be worn by the mammal Z. As shown in FIG. 1, the system can further comprise a receiving unit 20 for receiving and possibly processing data collected by the measuring unit 10, 10a, 10b. Alternatively, a receiving unit may be absent, and the measuring unit 10, 10a, 10b may be provided with means for reading out data, for example, a display or a terminal for a signal connector. The measuring unit 10, 10a, 10b may for instance be furthermore provided with data processing means for processing the measuring data and data storage means for storing the measuring data or results obtained therefrom by processing. Data storage means may also be provided for storing instructions for control of the measuring unit.

In FIG. 1 reference 10 schematically represents a first implementation in which the measuring unit has a first module 12 and second module 14 which are arranged on opposite sides of a skin part H (See FIG. 3) of the mammal Z. Alternatives include, for example, a single measuring unit 10a which is arranged on the skin, and a single measuring unit 10b which is arranged under the skin.

A practical implementation of the measuring unit 10 is shown in FIG. 2. In this embodiment, the first module 12 and second module 14 are suitable to be arranged on mutually opposite sides of an auricle of the mammal. In the implementation of FIG. 2 the two modules 12, 14 are shot one into the other for attachment.

As further shown schematically in FIG. 3, the first module 12 has a light source 122 for generating light L, an energy transmitting unit 126 and a control unit 125 for pulsewise activating the light source 122 and the energy transmitting unit 126.

The second module 14 is provided with a sensor unit 142 and a detector 148. The control unit 125, the energy transmitting unit 126 and the detector 148 jointly form synchronization means for pulsewise activating the sensor unit 142 synchronously with the light source 122. In the first module 12 a battery or other energy source (not shown) is included which supplies the electrical energy for the light source 122, the control unit 125 and the energy transmitting unit 126. The light source 122 is activated with control signal C1. The energy transmitting unit 126, upon activation by the control unit 125 with control signal C2, generates an electromagnetic field E. The detector 148 included in the second module 14 receives this electromagnetic field and generates therefrom a supply voltage, and also control signal C3 with which the sensor unit 142 is driven. In the embodiment shown, the sensor unit 142 and the light source 122 are synchronously activated with the aid of the energy transmitting unit 126 and the detector 148. In other words, the points of time at which the sensor unit 142 and the light source 122 are activated are mutually correlated. As a result, measuring can be done reliably also with a relatively short pulse duration. Moreover, the light source 122 and the sensor unit 142 can be fed from a common energy source. The activation points of time can coincide, but alternatively one of the activation points of time may be shifted by a predetermined time interval relative to the other activation point of time. It may be, for instance, that the sensor unit 142 has a start-up time between the moment of receiving an activation signal C3 from the detector 148 and the moment at which it becomes actually operational. It may also be that the sensor unit 142 after detecting the light pulse Lm needs some time for processing, storage or forwarding information. This can be allowed for in an embodiment in which the control unit 125 activates the control signal C2 in a time interval that begins before the time interval of activating the control signal C1 and that ends following the time interval of activating the control signal C1. Another solution would be for the light source 122 to be activated during a time interval that is long enough for the sensor unit to function properly. This provides the advantage that control is simpler. However, the energy consumption by the light source 122 is higher then.

In the embodiment shown, the light source 122 is an infrared LED or OLED, but if desired an LED may be used for generating light in a different part of the light spectrum, for example, in the visible range, or in the ultraviolet range. Also, conceivably, a different type of light source is used. An LED or OLED, however, is the most suitable for this purpose since this type of light source can be easily driven at relatively low voltages and with a short pulse duration.

The second module 14 has a sensor unit 142 for measuring an intensity of a fraction Lm of the generated light L, received via that skin part, for example the auricle.

The measured intensity depends on inter alia the extent to which light en route from the light source 122 to the sensor unit 142 is absorbed by the blood in the veins and capillaries in that skin part H. This, in turn, depends on inter alia the diameter of the veins and capillaries. The diameter varies periodically with the frequency of the heartbeat. Hence, also the measured intensity varies with that same frequency. In addition, depending on the wavelength of the light, the absorption may depend to a greater or lesser extent on the concentration of constituents in the blood. The sensor unit can thus determine the frequency of the heartbeat as a condition parameter of the mammal from the measured intensity variations.

FIG. 4 shows an embodiment of the sensor unit 142. In that embodiment, the sensor unit 142 is equipped with a sensor 1421, for example a photodiode, a frequency detector 1422 and a transmitter 1423. In operation, the sensor 1421 generates a signal $S_L$, which is indicative of an intensity of light from the light source 122 that is received by the sensor 1421 via the skin part H every time the light source 122 is pulsewise activated. The frequency detector 1422 receives a series of these signals and generates an output signal $S_F$ which is indicative of the frequency with which an envelope of the series is modulated. The transmitter 1423 forwards this signal to a receiver (e.g. element 20 in FIG. 1). In an embodiment, the sensor unit 142 is furthermore equipped with a data storage unit, e.g. a Flash memory or other type of memory. This makes it possible to store the established heartbeat data and forward the data batchwise. As there is less overhead then, the average use of electrical energy can be smaller than is the case in an embodiment where those data are forwarded individually. In another embodiment, a transmitter 1423 is absent and the data can be read out in a different manner, for instance, be read out from the data storage unit with a USB link or other link.

FIG. 5 shows another embodiment of the sensor unit 142. In this embodiment the sensor unit 142 has, instead of the frequency detector 1422, a signal filter 1424 which derives from the series of measuring signals $S_L$ a norm signal $S_G$. This norm signal is indicative of a value of the series of measuring signals which has been normalized for modulations present therein.

In the embodiment shown, the signal filter 1424 calculates an average value of the measuring values indicated by the series of measuring signals, the norm signal $S_G$ being indicative of the average value.

By determining the average value of a multiplicity of absorption measurements, the influence of the heartbeat on the measuring results is decimated. With, for instance, 100 measurements that are sufficiently uniformly distributed with respect to the phase of the heartbeat, the expected deviation in the end result due to the variations in the blood vessel width is decimated by a factor of 10. The measuring device is thus suitable for determining from the measuring signal $S_L$ a blood value as the condition parameter, or as one of the condition parameters of the mammal.

FIG. 6 shows yet another embodiment. In this embodiment the sensor unit has both a frequency detector 1422 and a signal filter 1424. The frequency detector 1422 moreover delivers in a predetermined phase a trigger signal Trigg. This trigger signal activates the signal filter 1424 to select in that predetermined phase a measuring signal $S_L$ for determination of the norm signal $S_G$.

For instance, the trigger signal can have the signal filter 1424 select a measuring signal at a moment at which the blood pressure value is between the minimum and the maximum value. Alternatively, the trigger signal can have the signal filter 1424 select measuring signals at a number of moments in the heartbeat cycle, with the signal filter then calculating an average value of the measuring values indicated by the measuring signals at those moments. The measuring device is thus suitable both for determining a blood value from the measuring signal $S_L$ and for determining a heartbeat from the measuring signal $S_L$ as the condition parameter or as one of the condition parameters of the mammal.

FIG. 7 schematically shows components of an alternative embodiment of the measuring unit of FIG. 2. In this embodiment, the measuring unit 10 is provided with synchronization means for pulsewise activating the second module 14 synchronously with the light source 122. In the embodiment shown, the synchronization means comprise an energy transmitting unit 144 which is part of the second module 14 and a detector 124 which is part of the first module 12. The second module 14 is provided with a control unit 145 which activates the energy transmitting unit 144 and the sensor unit 142 at the same time. Also, in the second module 14 a battery (not shown) is included which furnishes the electrical energy for the sensor unit 142, the control unit 145 and the energy transmitting unit 144. Upon activation by the control unit 145, the energy transmitting unit 144 generates an electromagnetic field E. The detector 124 included in the first module 12 receives this electromagnetic filed and generates therefrom a supply voltage with which the light source 122 is driven. In the embodiment shown, the sensor unit 142 and the light source 122 are activated simultaneously with the aid of the energy transmitting unit 144 and the detector 124. As a consequence, measuring can be done reliably also with a relatively short pulse duration. Moreover, a separate supply for the light source 122 and for the sensor unit is superfluous. In another embodiment, the energy transmitting unit and the control unit may be included in the first module and the detector in the second module, as discussed with reference to FIG. 3. The embodiment of FIG. 7, however, is more favorable because it is expected that on average less energy needs to be transferred from the second to the first module than would have to be transferred from the first to the second module in that other embodiment. Thus, energy losses often entailed in a wireless transfer are smaller as well.

The control unit 145 can be, for example, a programmable microprocessor, a configurable processor which is configured for this purpose, dedicated hardware (ASIC), or a combination of these options. The control unit 145 may in addition be deployed for processing the measuring data furnished by the sensor 142. The control unit 145 may then be integrated in the sensor unit 142. As shown, for example, in FIGS. 4-6, the sensor unit 142 may, in a variant, actively transmit the measuring data or the results obtained therefrom to a receiving unit 20 (See FIG. 1). In another variant, the data and/or results obtained therefrom can be read out by querying, for example with an RFID transmitter (not shown). In that case, the RFID transmitter generates an interrogation field which is detected and modulated by an RFID detector included in the second module, which modulates the interrogation field in accordance with the data or results to be queried. The RFID transmitter detects these modulations and reconstructs from them the data or results to be queried. The RFID detector may also be designed to draw energy from the interrogation field, to supply the measuring unit 10, or components thereof, with it. In both variants, also a receiving module may be included in the measuring unit 10, 10a, 10b, for instance to transfer software for the control unit 145 to the measuring unit 10, 10a, 10b or to adapt settings of the measuring unit 10, 10a, 10b.

FIG. 8 shows a practical elaboration of the embodiment of FIG. 7. There, in the second module 14, the series connection with capacitor $C_1$, coil $L_1$ and resistance $R_1$ constitutes a first damped resonance circuit which is driven by alternating voltage source $V_1$. The alternating voltage source $V_1$ is activated pulsewise by the control unit 145. A coil $L_2$ of the first module 12 is inductively coupled with coil $L_1$ in the second module 14, for receiving the electromagnetic field E generated by the coil $L_1$. The series connection of resistance $R_2$, coil $L_2$ and capacitor $C_2$ forms a second resonance circuit with a corresponding resonance frequency to that of the first resonance circuit. With the aid of a detector circuit formed by diode $D_1$, capacitor $C_2$, coil $L_3$ and capacitor $C_3$, a supply voltage $V_L$ is generated from field E for feeding the light source 122, here implemented as an (O)LED. It will be clear that also other practical elaborations are possible. For instance, provision may be made for a capacitive instead of an inductive coupling between the modules 12, 14. Also, other detector circuits, known to the skilled person, may be used. It is furthermore conceivable that, instead of the LED, another light source, such as an incandescent lamp or a discharge lamp, is used. However, a LED is preferred in view of its relatively high efficiency and relatively low supply voltage.

Figure 9A:
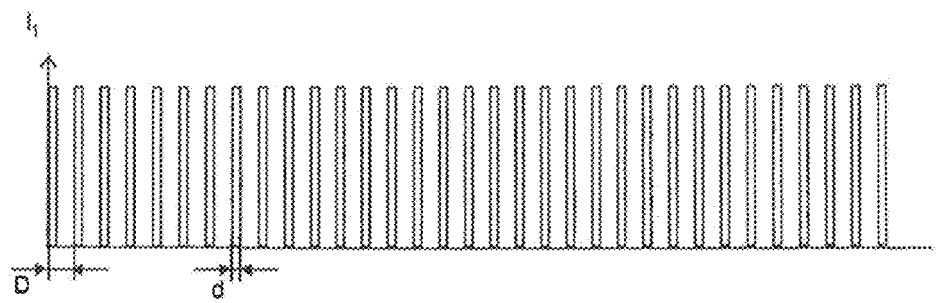
Figure 9B:
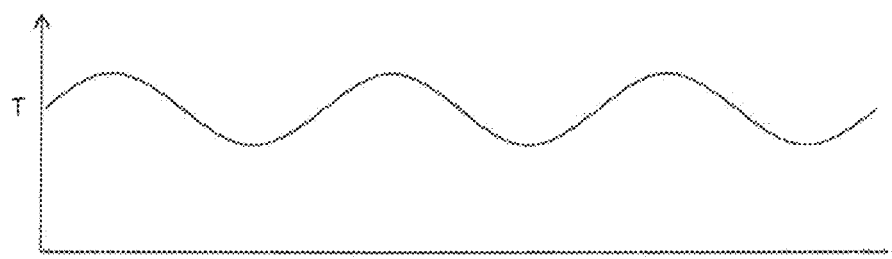
Figure 9C:
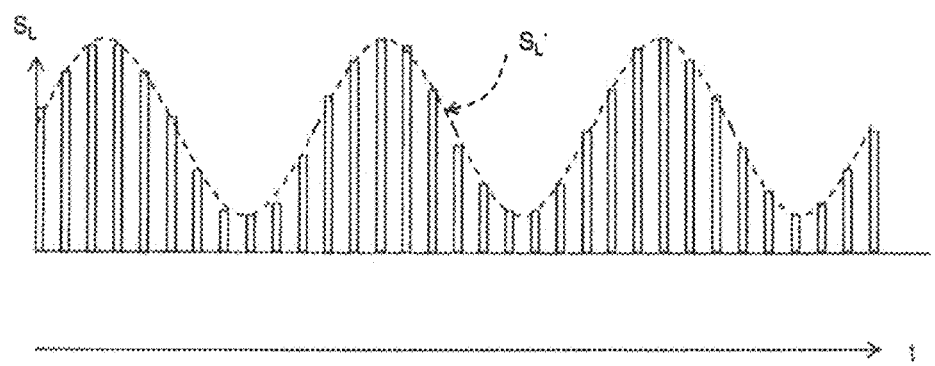

FIGS. 9A, 9B, and 9C schematically show a measuring method for measuring physiological data of a mammal.

The measuring method comprises pulsewise generating light of a known intensity $I_1$ on a side of a skin part H of the mammal. This is shown in FIG. 9A. In this embodiment the pulses have a pulse duration d and a pulse period D. The ratio of pulse duration to pulse period d/D may in practice differ from the ratio suggested by the drawing. In an embodiment, the pulse period is, for example, in the order of 0.01 to 0.5 seconds and the pulse duration is, for example, in the order of 1 microsecond to 100 microseconds.

FIG. 9B schematically shows the transmission of the skin for the light used in the measuring method. The transmission varies in time as a result of the variation of the blood pressure in the rhythm of the heartbeat, which, depending on the condition of the animal, can be 60 to 180 beats per minute.

On a second, opposite side of the skin part, an intensity is measured of a fraction (Lm), received via that skin part, of the pulsewise generated light, as shown in FIG. 9C. A measuring signal $S_L$ is delivered that is indicative of the value of the intensity measured during pulsewise activation.

FIG. 9C also shows, in addition to the observed pulsewise varying intensity, as indicated by signal $S_L$, an envelope $S_L'$. This signal is indicative of the light transmission of the skin part, and varies with the rhythm of the heartbeat.

With the aid of a frequency detector, e.g. detector 1422 as shown in FIG. 4 or FIG. 6, the frequency of the heartbeat as a condition parameter of the mammal is established from the envelope $S_L'$.

In an embodiment, from the series of measuring signals $S_L$, a norm signal $S_G$ is derived that is indicative of a value of the series of measuring signals that has been normalized for modulations present therein.

The norm signal $S_G$ can be indicative of the blood pressure of the mammal. Thus, the blood pressure as a condition parameter of the mammal can be determined. According as the blood pressure is higher, the width of blood vessels in the skin part increases and the light transmission decreases. With, for example, a zero measurement, it can be established what value the norm signal has at a particular blood pressure of the mammal, so that thereafter, on the basis of the norm signal, it can be established whether the current value of the blood pressure is below or above that particular value. Also, with a series of measurements the interrelatedness between the blood pressure and the measuring signal can be established, for example by recording how the measuring signal varies as a result of the blood pressure variations during a heartbeat cycle.

The light transmission further depends on the composition of the blood. With this, the blood pressure as a condition parameter of the mammal can be determined. In an embodiment, see for example FIG. 3A, the light source 122 of the first module 12 may be provided with different light source elements 122₁, 122₂, . . . , 122ₙ for generating light in mutually different wavelength bands, which may or may not overlap. The sensor unit 142 of the second module 14 may be provided with different sensor elements to establish to what extent light is transmitted in each of those wavelength bands by the skin part. Alternatively, it is possible for a single sensor element to suffice, provided that the light source elements in operation are activated separately from each other. For instance, the light source elements may be activated one after the other in mutually non-overlapping time intervals so that a multiplicity of received signals are obtained (for example, one per light source). Upon activation of each light source element, it can then be established with the single sensor element to what extent light originating from that light source element is transmitted by the skin part. As the light sources have mutually different frequency spectra, on the basis of the various received signals per light source, in combination, more information or more accurate information about the animal can be obtained than with a single received signal. Also, it is conceivable for the time intervals to be chosen such as to overlap each other partly. In that case, the amount of transmitted light can be established both for the light source elements separately and for a combination of light source elements. It is even conceivable that the light source elements are activated both separately and in any possible combination, and the amount of transmitted light is measured. In yet another embodiment, provision is made for a light source having a single light source element and a plurality of sensor elements that are sensitive to mutually different wavelength bands within the spectrum of the light generated by the single light source element.

In this document the indefinite article "a(n)" is used in the sense of "one or more", as is conventional in patent documents. The wording "comprises" is not used exclusively. In other words, if in this document it is stated that a first element comprises a second element, the first element may also include other elements besides the second element. Furthermore, in this document the term "or" is used in a non-exclusive sense. That is to say, "A or B" covers "A but not B", "B but not A", and "A and B", unless indicated otherwise.

The invention claimed is:

1. A measuring device for measuring physiological data of a mammal for determining at least one condition parameter of the mammal, comprising: a measuring unit, to be worn by the mammal, with a first and second module configured to be arranged opposite a skin part of the mammal, which first module comprises a light source for generating light and which second module comprises a sensor for measuring an intensity of a fraction of the light received via that skin part and for delivering a measuring signal which is indicative of the measured value of the intensity, wherein the first module and second module are designed to be arranged mutually on opposite external sides of the skin part, wherein the measuring device is designed for pulsewise activating the light source, wherein the measuring signal is indicative of the value of the intensity measured during the pulsewise activation, wherein the measuring device is furthermore provided with synchronization means for synchronously activating the light source and the second module, wherein the synchronization means comprises a controller, an energy transmitter which is part of one of the first and the second module, and a detector which is part of the other one of the first and the second module, wherein in an operating condition the energy transmitter pulsewise generates an electromagnetic field responsive to the controller, and the detector receives this field and generates therefrom a supply voltage for use in that other module.

2. The measuring device according to claim 1, wherein the controller pulsewise activates the light source and the energy transmitter, wherein the detector pulsewise activates the sensor in response to the energy that is received from the energy transmitter or that the controller pulsewise activates the sensor and the energy transmitter, wherein the detector pulsewise activates the light source in response to the energy that is received from the energy transmitter.

3. The measuring device according to claim 2, wherein the energy transmitter is part of the second module and that the detector is part of the first module to pulsewise activate the light source therewith.

4. The measuring device according to claim 1, wherein the controller is configured for a repeated pulsewise activation with a pulse period that is longer than the pulse duration, wherein the sensor delivers a series of measuring signals that are indicative of the intensity measured during each activation.

5. The measuring device according to claim 4, wherein the second module furthermore comprises a frequency detector for measuring a frequency of an envelope of the series of measuring signals and for delivering a frequency signal that is indicative of the measured frequency.

6. The measuring device according to claim 5, wherein the frequency detector is configured for, in a predetermined phase of the envelope, delivering a trigger signal, which trigger signal in that predetermined phase activates the signal filter to select a measuring signal for determination of the norm signal.

7. The measuring device according to claim 4, wherein the second module furthermore comprises a signal filter which derives from the series of measuring signals a norm signal, which norm signal is indicative of a value of the series of measuring signals that has been normalized for modulations present therein.

8. The measuring device according to claim 7, wherein the signal filter determines from the series of measuring signals an average value as the norm signal.

9. The measuring device according to claim 1, wherein the measuring unit is configured for determining from the measuring signal the at least one condition parameter, wherein the at least one condition parameter comprises at least a heartbeat of the mammal.

10. The measuring device according to claim 1, wherein the measuring unit is configured for determining from the measuring signal the at least one condition parameter, wherein the at least one condition parameter comprises at least a blood value of the mammal.

11. The measuring device according to claim 1, wherein the light source of the first module is provided with different light source elements for generating light in mutually different wavelength bands.

12. The measuring device according to claim 11, wherein the controller is configured to activate the different light source elements of the light source at mutually different points of time so that in succession a plurality of received signals are obtained which are processed in combination for determining the at least one condition parameter of the mammal.

13. The measuring device according to claim 1, wherein the light source comprises one or more LEDs.

14. A measuring method for measuring physiological data of a mammal for determining at least one condition parameter of the mammal, comprising: generating light opposite an external skin part of the mammal, measuring on an opposite external side of that skin part an intensity of a fraction of the generated light received via that skin part, delivering a measuring signal that is indicative of the measured value of the intensity, wherein the light is pulsewise generated, wherein the measuring signal is indicative of the value of the intensity measured during the pulsewise activation, wherein pulsewise generating the light and measuring on the opposite side of that skin part the fraction of the generated light received via the skin part are done synchronously by pulsewise generating an electromagnetic field, receiving the electromagnetic field, and generating a supply voltage from the received electromagnetic field.

15. The measuring method according to claim 14, wherein the supply voltage is used for generating the light or measuring the intensity.

16. The measuring method according to claim 14, wherein the pulsewise generating comprises a repeated pulsewise activation with a pulse period that is longer than the pulse duration, wherein a series of measuring signals is delivered that are indicative of the intensity measured during each activation.

17. The measuring method according to claim 16, furthermore comprising measuring a frequency of an envelope of the series of measuring signals and delivering a frequency signal that is indicative of the measured frequency.

18. The measuring method according to claim 16, furthermore comprising deriving from the series of measuring signals a norm signal, which norm signal is indicative of a value of the series of measuring signals that has been normalized for modulations present therein.

19. The measuring method according to claim 18, comprising calculating an average value of measuring values indicated by the series of measuring signals, wherein the norm signal is indicative of the average value.

20. The measuring method according to claim 18, wherein the measuring signal is part of a set of measuring signals, wherein respective measuring signals in the set of measuring signals are indicative of respective values of a measured intensity in mutually different wavelength bands of the generated light.

21. The measuring method according to claim 18, comprising, in a predetermined phase of the envelope, delivering a trigger signal, with which trigger signal a measuring signal is selected from the series of measuring signals for determination of the norm signal.

22. The measuring method according to claim 14, further comprising determining from the measuring signal the at least one condition parameter, wherein the at least one condition parameter comprises at least a heartbeat of the mammal.

23. The measuring method according to claim 14, further comprising determining from the measuring signal the at least one condition parameter, wherein the at least one condition parameter comprises at least a blood value of the mammal.

24. The measuring method according to claim 14, wherein generating light comprises generating light in mutually different wavelength bands at mutually different points of time so that successively a plurality of received signals are obtained.

25. The method according to claim 24, wherein the successively obtained received signals can be processed in combination for determining the at least one condition parameter of the animal.

26. The measuring method according to claim 14, wherein generating light is done with at least an LED.

* * * * *